United States Patent
Hirose et al.

(10) Patent No.: US 10,851,343 B2
(45) Date of Patent: Dec. 1, 2020

(54) METHOD FOR PRODUCING PURIFIED PLATELETS

(71) Applicant: Megakaryon Corporation, Kyoto (JP)

(72) Inventors: Hidenori Hirose, Kyoto (JP); Michiko Ueda, Kyoto (JP)

(73) Assignee: Megakaryon Corporation, Kyoto (JP)

(*) Notice: Subject to any disclaimer, the term of this patent is extended or adjusted under 35 U.S.C. 154(b) by 0 days.

(21) Appl. No.: 15/763,705

(22) PCT Filed: Oct. 14, 2016

(86) PCT No.: PCT/JP2016/080553
§ 371 (c)(1),
(2) Date: Mar. 27, 2018

(87) PCT Pub. No.: WO2017/065280
PCT Pub. Date: Apr. 20, 2017

(65) Prior Publication Data
US 2018/0282697 A1 Oct. 4, 2018

(30) Foreign Application Priority Data
Oct. 14, 2015 (JP) .................................. 2015-203275

(51) Int. Cl.
C12N 5/078 (2010.01)
A61K 35/19 (2015.01)
(Continued)

(52) U.S. Cl.
CPC ............ C12N 5/0644 (2013.01); A61K 35/14 (2013.01); A61K 35/19 (2013.01); B01D 21/262 (2013.01);
(Continued)

(58) Field of Classification Search
None
See application file for complete search history.

(56) References Cited

U.S. PATENT DOCUMENTS 6,315,706 B1 11/2001 Unger et al.
2006/0099198 A1* 5/2006 Thomson ............. C12N 5/0644
424/93.72
(Continued)

FOREIGN PATENT DOCUMENTS

| EP | 2163261 A1 | 3/2010 |
| JP | H08131539 A | 5/1996 |

(Continued)

OTHER PUBLICATIONS

European Search Opinion received in EP16855533 dated May 28, 2019.
(Continued)

*Primary Examiner* — Erin M. Bowers
(74) *Attorney, Agent, or Firm* — Suzannah K. Sundby, Esq.; Canady + Lortz LLP

(57) ABSTRACT

The present invention provides a method for producing purified platelets from a culture of megakaryocytes, comprising a first centrifugal separation step of centrifugally separating the culture at a centrifugal force of 150×g to 550×g, and a second centrifugal separation step of centrifugally separating, at a centrifugal force of 600×g to 4000×g, a liquid component recovered in the first centrifugal separation step.

19 Claims, 5 Drawing Sheets

MEASUREMENT OF PLATELET COUNT

BEFORE PURIFICATION
(OFF CULTURING)

PLATELETS AFTER PURIFICATION

(51) Int. Cl.
  *C12N 1/02*   (2006.01)
  *C12N 15/09*  (2006.01)
  *A61K 35/14*  (2015.01)
  *B01D 21/26*  (2006.01)
  *B04B 7/14*   (2006.01)

(52) U.S. Cl.
  CPC ............... *B04B 7/14* (2013.01); *C12N 1/02* (2013.01); *C12N 15/09* (2013.01)

(56) References Cited

U.S. PATENT DOCUMENTS

| | | | |
|---|---|---|---|
| 2009/0074737 A1* | 3/2009 | Rosiello | A61K 35/19 424/93.72 |
| 2012/0294842 A1 | 11/2012 | Liu et al. | |
| 2012/0315338 A1 | 12/2012 | Li et al. | |
| 2014/0127815 A1* | 5/2014 | Eto | A61K 35/19 435/467 |
| 2014/0271590 A1 | 9/2014 | Feng et al. | |
| 2015/0182588 A1 | 7/2015 | Kahvejian et al. | |
| 2016/0324897 A1 | 11/2016 | Ingber et al. | |

FOREIGN PATENT DOCUMENTS

| | | |
|---|---|---|
| JP | H09108594 A | 4/1997 |
| JP | 2005-296675 * | 10/2005 |
| JP | 2009511069 A | 3/2009 |
| JP | 2013512676 A | 4/2013 |
| JP | 2014515352 A | 6/2014 |
| WO | 2006050330 A2 | 5/2006 |
| WO | 2007047687 A2 | 4/2007 |
| WO | 2011069127 A1 | 6/2011 |
| WO | 2012157586 A1 | 11/2012 |
| WO | 2014055988 A1 | 4/2014 |
| WO | 2015109220 A1 | 7/2015 |
| WO | 2015146415 A1 | 10/2015 |
| WO | 2015153102 A1 | 10/2015 |

OTHER PUBLICATIONS

Amable et al., "Platelet-rich plasma preparation for regenerative medicine: optimization and quantification of cytokines and growth factors", Jun. 7, 2013, p. 67 vol. 4, No. 3, Publisher: Stem Cell Res Ther.

Araki et al., "Optimized preparation method of platelet-concentrated plasma and noncoagulating platelet-derived factor concentrates: maximization of platelet conc . . . ", Nov. 22, 2011, pp. 176-185, vol. 18, No. 3, Publisher: Tissue Eng Part C Methods.

Dhurat et al., "Principles and Methods of Preparation of Platelet-Rich Plasma: A Review and Author's Perspective", Jan. 1, 2014, pp. 189-197, vol. 7, No. 4, Publisher: J Cutan Aesthet Surg.

Li et al., "In vitro differentiation of umbilical cord blood CD 34+ cells into mature megakaryocytes and generation of platelets", Apr. 21, 2009, p. 1976-1980, vol. 13, No. 10, Publisher: Journal of Clinical Rehabilitative Tissue Engineering Research.

Schlinker, et al., "Separation of in-vitro-derived megakaryocytes and platelets using spinning-membrane filtration : Separation of In-Vitro-Derived Platelets", Apr. 1, 2015, p. 788-800, vol. 112, No. 4, Publisher: Biotechnology and Bioengineering.

International Search Report received in PCT/JP2016/080553 dated Jan. 17, 2017.

Written Opinion received in PCT/JP2016/080553 dated Jan. 17, 2017.

* cited by examiner

MEASUREMENT OF UNUSUAL PLATELETS

ANNEXIN V

METHOD FOR PRODUCING PURIFIED PLATELETS

TECHNICAL FIELD

The present invention relates to a method for producing purified platelets from a culture of megakaryocytes.

BACKGROUND ART

Platelet preparations are administered to patients presenting with large-volume blood loss during surgery or trauma or bleeding tendencies associated with thrombocytopenia following anticancer therapy, for the purpose of treating and preventing the symptoms. At present, platelet preparations are dependent on blood donations from healthy volunteers. However, the number of blood donors in Japan has decreased due to changes in the population structure, and there is estimated to be a shortage of roughly 1 million blood donations by the year 2027. Thus, ensuring a stable supply of platelets is an important issue in the art.

In addition, since conventional platelet preparations harbor a high risk of bacterial infection, there is the potential for platelet preparations to cause serious infections following the transfusion thereof. Consequently, there is constantly a need for safer platelet preparations in the clinical setting. In order to respond to this need, a method has currently been developed for producing platelets from megakaryocytes cultured in vitro.

When transfusing a platelet preparation, there are rare cases in which this transfusion causes a transfusion reaction (such as hives or an anaphylactic reaction). Plasma contained in the platelet preparation is thought to be one of the causes. Therefore, in order to prevent such transfusion reactions, a method has been developed by which the plasma present in a platelet preparation is replaced with an artificially prepared liquid (wash/storage solution). For example, one method involves washing platelets using a centrifugal separator equipped with a separation bowl for washing platelets of platelet concentrates. A platelet concentrate as referred to here refers to that obtained by collecting blood components, removing the majority of leukocytes, and suspending the harvested platelets in plasma.

On the other hand, in the case of producing platelets by culturing megakaryocytes in vitro, it is necessary to separate and concentrate the platelets from megakaryocytes. Since they cannot be separated with a cell sorter since both have the same surface markers, a method involving separating with a filter or hollow fiber membrane by utilizing the difference in size, or a method involving centrifugal separation using a centrifuge tube, has been used to separate platelets and megakaryocytes. However, in the case of methods using a filter or hollow fiber membrane, in addition to the platelets losing physiological activity due to damage to surface proteins, the platelet recovery rate is low at only about 10%. In addition, methods using centrifugal separation have the problems of a low megakaryocyte removal rate as a result of employing a low centrifugation speed to prevent decreases in function, a low platelet recovery rate of about 10%, and the amount of platelets that can be purified at one time being limited by the volume of the centrifuge tube.

SUMMARY

Technical Problem

An object of the present invention is to provide a method for producing high-quality purified platelets from a culture of megakaryocytes by separating and purifying a large amount of platelets in a single batch and at a high recovery rate.

Solution to Problem

As a result of conducting extensive studies to solve the above-mentioned problems, the inventors of the present invention found that high-quality platelets can be purified at a high recovery rate from a culture of megakaryocytes by subjecting the culture of megakaryocytes to centrifugation treatment at a prescribed centrifugal force followed by repeating centrifugation treatment on the liquid component obtained with the above-mentioned centrifugation treatment at a higher centrifugal force.

Namely, the present invention relates to that indicated below.

[1] A method for producing purified platelets from a culture of megakaryocytes, which comprises:
a first centrifugal separation step of centrifugally separating the culture at a centrifugal force of 150×g to 550×g; and
a second centrifugal separation step of centrifugally separating, at a centrifugal force of 600×g to 4000×g, a liquid component recovered in the first centrifugal separation step.

[2] The method described in [1], wherein the centrifugal separation steps are carried out with a centrifugal separator provided with: a rotatable separation bowl provided with an inner wall, to which substances having a high specific gravity adhere corresponding to centrifugal force, and an outflow port through which a liquid component flows following separation; and recovery means for recovering the liquid component that has flown out from the outflow port.

[3] The method described in [2], which comprises:
a washing step of adding a wash solution to the separation bowl followed by rotating after the second centrifugal separation step; and
a platelet recovery step of adding a recovery solution followed by rotating after the washing step.

[4] The method described in [2] or [3], wherein, in the first centrifugal separation step, the culture is injected into the separation bowl by allowing the culture to drop therein by gravity.

[5] The method described in any one of [1] to [4], wherein the culture of megakaryocytes is obtained by the steps of:
overexpressing a cancer gene and a Polycomb gene in cells less differentiated than megakaryocytes;
overexpressing a Bcl-xL gene in the cells; and
terminating all the overexpression.

[6] A method for producing a blood preparation, which comprises: a step of mixing purified platelets produced using the method described in any one of [1] to [3] above, with another component.

Advantageous Effects of Invention

According to the method of the present invention, since high-quality platelets can be purified from a culture of megakaryocytes in a single batch and at a high recovery rate, safe platelet preparations having low risk of bacterial contamination can be produced and supplied in large amounts.

DESCRIPTION OF EMBODIMENTS

Figure 1:
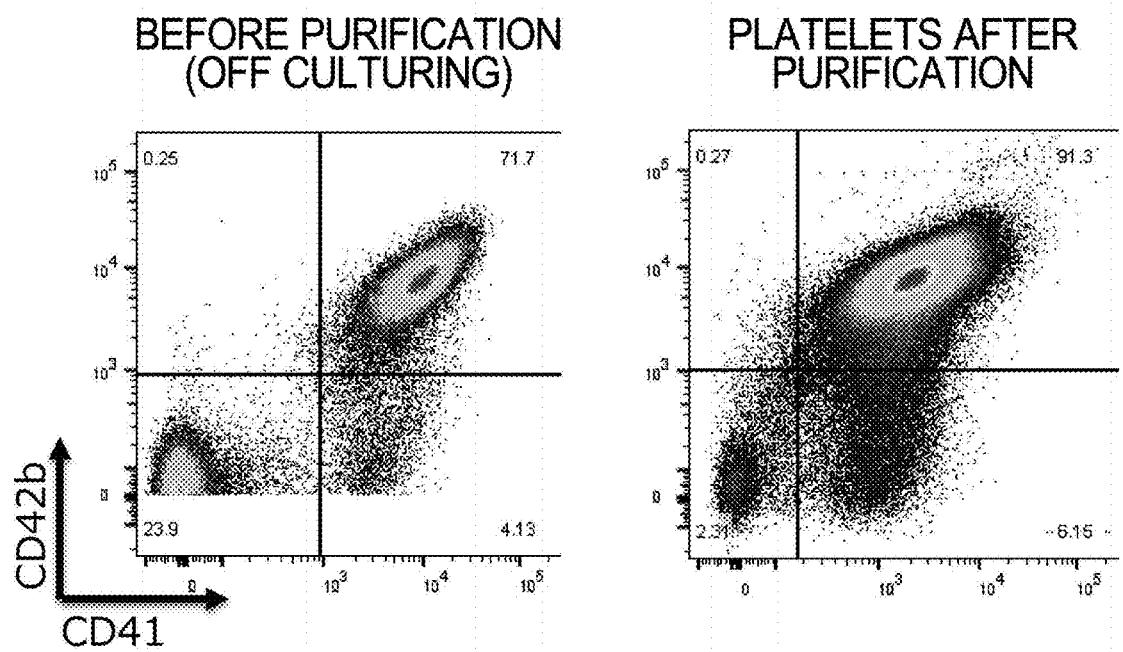
FIG. 1 indicates the results of measuring platelet counts before and after purification by the purification method according to the present invention.

The method for producing platelets according to the present invention comprises two or more centrifugal separation steps for centrifugally separating a sample containing megakaryocytes at different centrifugal forces. For example, a first centrifugal separation step can be carried out at a centrifugal force of about 150×g to about 550×g, and a second centrifugal separation step can be carried out at a centrifugal force of about 600×g to about 4000×g. The centrifugal separation steps may be carried out with a centrifugal separator provided with: a rotatable separation bowl provided with an inner wall, to which substances having a high specific gravity adhere corresponding to centrifugal force, and an outflow port through which a liquid component flows following separation; and recovery means for recovering the liquid component that has flown out from the outflow port.

In this centrifugal separator, when a liquid mixture is injected while rotating the separation bowl about an axis passing through and perpendicular to the bottom thereof, components having a high specific gravity adhere to and are deposited on the inner wall of the separation bowl corresponding to centrifugal force, while components having a low specific gravity remain in the liquid.

Liquid containing components having a low specific gravity are recovered by recovery means. The recovery means is composed of, for example, a tube connected to an outflow port of the separation bowl, and a recovery bag replaceably connected to the tube. There are no particular limitations on the recovery bag provided it does not have an effect on platelet quality, and a commercially available bag for storing blood or blood components may be used.

Since the centrifugal separator is able to carry out centrifugal separation while injecting a liquid mixture into the separation bowl at a prescribed rate and recover the simultaneously separated liquid with the recovery means, a large amount of the liquid mixture can be separate continuously regardless of the volume of the separation bowl.

Examples of centrifugal separators able to be used in the purified platelet production method according to the present invention include the device disclosed in Patent Publication JP-A-2005-296675 and the device disclosed in Patent Publication JP-A-H07-284529. In addition, a commercially available centrifugal separator used to separate blood components or a commercially available device used to wash platelets of platelet concentrations may also be used. For example, the ACP215 system manufactured by Haemonetics Corporation or the COBE2991 system manufactured Terumo Corporation may be used.

In a specific aspect of the present invention, the first centrifugal separation step may be carried out by rotating the separation bowl at a centrifugal force of about 150×g to about 550×g. This centrifugal force is preferably about 160×g to about 500×g, more preferably about 170×g to about 400×g, and more preferably about 180×g to about 300×g. Megakaryocytes present in the culture adhere to and are deposited on the inner wall of the separation bowl by carrying out centrifugal separation with centrifugal force within these ranges. If centrifugal force is increased beyond these ranges, shear stress acts on the platelets causing the physiological activity of the platelets to be expressed resulting in aggregation.

Furthermore, since the following relationship exists among centrifugal force (g), rotating speed (rpm) and radius of rotation (cm), rotating speed can be determined according to the size of the rotating bowl used.

$$\text{Centrifugal force(g)}=1119 \times \text{radius of rotation (cm)} \times (\text{rotating speed (rpm)})^2 \times 10^{-8}$$

In this step, a platelet storage solution may be added to the culture of megakaryocytes. An example thereof is Biological Products Standard Blood Storage Solution A (Acid-Citrate-Dextrose: ACD-A). ACD-A has blood and platelet anticoagulant action and also functions as a supply source of glucose, which is used as an energy source by platelets.

During the first centrifugal separation step, there are no particular limitations on the method used to inject the culture of megakaryocytes into the separation bowl, and a pump provided with the device may be used, or a vessel containing the culture and the separation bowl may be connected with a tube, the vessel may be suspended at a higher location than the separation bowl, and the culture may be allowed to drop into the bowl by gravity through the tube. The injection rate can be, for example, about 50 ml/min to about 150 ml/min, about 80 ml/min to about 130 ml/min, or about 100 ml/min.

The first centrifugal separation step can be carried out at room temperature. The duration of the first centrifugal separation step can be equal to or greater than the amount of time obtained by dividing the volume of the culture by the culture injection rate.

In the first centrifugal separation step, platelets remain in solution and are recovered by the recovery means.

The second centrifugal separation step of the method for purifying platelets according to the present invention is a step of separating platelets from a liquid component recovered in the first centrifugal separation step.

After the first centrifugal separation step, the liquid component recovered in the first centrifugal separation step is injected while rotating the separation bowl after having replaced or washed the separation bowl. Injection can be carried out in the same manner as in the first centrifugal separation step. The recovery bag used in the first centrifugal separation step is suspended as is from a high location, and the liquid component may be injected into the separation bowl by allowing the liquid component to drop by gravity through a tube.

In a specific aspect of the present invention, the second centrifugal separation step may also be carried out by rotating the separation bowl at a centrifugal force of about 600×g to about 4000×g. This centrifugal force may be preferably about 800×g to about 3000×g and more preferably about 1000×g to about 2000×g. Platelets can adhere to and be deposited on the inner wall of the separation bowl without undergoing a loss of physiological activity by carrying out centrifugal separation with centrifugal force within these ranges.

The second centrifugal separation step can be carried out at room temperature. The duration of the first centrifugal separation step can be equal to or greater than the amount of time obtained by dividing the volume of the liquid component recovered in the first centrifugal separation step by the liquid injection rate.

The liquid component separated in the second centrifugal separation step is recovered and discarded by the recovery means.

In another aspect, a washing step may be carried out after the second centrifugal separation step. In the second centrifugal separation step, medium and additives adhere to and are deposited on the inner wall of the separation bowl together with platelets. The washing step is carried out to remove this medium.

In the washing step, a wash solution is added to the separation bowl followed by rotating at a centrifugal force of about 600×g to about 3600×g. A bicarbonate Ringer's solution such as Bicarbon may be used for the wash solution. In addition, a platelet storage solution may be added to the Bicarbon. ACD solution, for example, may be added for the platelet storage solution. Furthermore, the wash solution is injected at a constant rate when adding wash solution to the separation bowl. At this time, platelets are maintained adhered to the inner wall of the separation bowl, and wash solution containing medium and additives is recovered by the recovery means.

In another aspect, a platelet recovery step may be carried out after the washing step. In the recovery step, a recovery solution is added for recovering platelets adhered to the inner wall of the separation bowl followed by rotating at centrifugal force of about 600×g to about 3600×g. As a result, the platelets are shaken off from the separation bowl and suspended in the recovery solution. Bicarbon, for example, can be used for the recovery solution, and this is injected into the separation bowl at a constant rate. 5% ACD may be added to the Bicarbon. Recovery solution containing platelets flows out from the outflow port of the separation bowl and is recovered in a recovery bag or other recovery means. This can then be used as the finished product.

In the present description, a "megakaryocyte" refers to the largest cell present in bone marrow of the body and is characterized by releasing platelets. Megakaryocytes are characterized by being positive for cell surface markers CD41a, CD42a and CD42b, and may further express markers selected from the group consisting of cell surface markers CD9, CD61, CD62p, CD42c, CD42d, CD49f, CD51, CD110, CD123, CD131 and CD203c. When megakaryocytes become multinucleated (polyploidal), they have a genome equal to 16 to 32 times the genome of normal cells. In the present description, in the case of simply referring to "megakaryocytes", both multinucleated megakaryocytes and pre-multinucleated megakaryocytes are included provided they have the above-mentioned characteristics. "Pre-multinucleated megakaryocytes" have the same meaning as "immature megakaryocytes" or "growth phase megakaryocytes".

Megakaryocytes can be obtained by various known methods. A non-limiting example of a method for producing megakaryocytes is the method described in WO 2011/034073. In this method, an infinitely proliferating immortalized megakaryocyte cell line can be obtained by overexpressing a cancer gene or Polycomb gene in "cells less differentiated than megakaryocytes". In addition, according to the method described in WO 2012/157586, an immortalized megakaryocyte cell line can be obtained by overexpressing an apoptosis suppressor gene in "cells less differentiated than megakaryocytes". These immortalized megakaryocyte cell lines can be made to multinucleate and release platelets by terminating overexpression of gene.

In order to obtain megakaryocytes, the above-mentioned methods described in the literature may also be combined. In that case, overexpression of a cancer gene, Polycomb gene or apoptosis suppressor gene may be carried out simultaneously or sequentially. For example, multinucleated megakaryocytes may be obtained by overexpressing a cancer gene and Polycomb gene, suppressing that overexpression, overexpressing an apoptosis suppressor gene and finally suppressing that overexpression. In addition, multinucleated megakaryocytes can also be obtained by simultaneously overexpressing a cancer gene, Polycomb gene and apoptosis suppressor gene followed by simultaneously suppressing the overexpression thereof. Alternatively, multinucleated megakaryocytes can be obtained by first overexpressing a cancer gene and Polycomb gene followed by overexpressing an apoptosis suppressor gene, and then simultaneously suppressing the overexpression of all three genes.

In the present description, "cells less differentiated than megakaryocytes" refer to cells having the ability to differentiate into megakaryocytes in one of the various stages of differentiation from hematopoietic stem cells to megakaryocytes. Non-limiting examples of cells less differentiated than megakaryocytes include hematopoietic stem cells, hematopoietic progenitor cells, CD34-positive cells, and megakaryocyte-erythroid progenitor (MEP) cells. These cells can be isolated and obtained from, for example, bone marrow, umbilical cord blood or peripheral blood, and can be obtained by inducing to differentiate from less differentiated cells in the form of pluripotent stem cells such as ES cells or iPS cells.

In the present description, a "cancer gene" refers to a gene that induces a malignant transformation in cells of the body, and examples thereof include MYC family genes (such as c-MYC, N-MYC or L-MYC), SRC family genes, RAS family genes, RAF family genes, and protein kinase family genes such as c-Kit, PDGFR or Abl.

In the present description, a "Polycomb gene" is known to be a gene that functions to avoid cellular senescence by negatively controlling CDKN2a (INK4a/ARF) gene (Okura, et al., Regenerative Medicine, Vol. 6, No. 4, pp. 26-32; Jseus et al., Jseus et al., Nature Reviews Molecular Cell Biology, Vol. 7, pp. 667-677, 2006; Proc. Natl. Acad. Sci. USA, Vol. 100, pp. 211-216, 2003). Non-limited examples of Polycomb genes include BMI1, MeL18, Ring1a/b, Phc1/2/3, Cbx2/4/6/7/8, Ezh2, Eed, Suz12, HADC and Dnmt1/3a/3b.

In the present description, an "apoptosis suppressor gene" refers to a gene having a function that suppresses cellular apoptosis, and examples thereof include BCL2 gene, BCL-xL gene, Survivin gene and MCL1 gene.

Forced expression of a gene and termination of overexpression can be carried out by the methods described in WO 2011/034073, WO 2012/157586, WO 2014/123242, the method described in Nakamura, S., et al., Cell Stem Cell, 14, 535-548, 2014 or other known methods.

In the present description, "platelets" are characterized by being one of the cellular components of blood that are CD41a-positive and CD42b-positive. In addition to fulfilling the important roles of thrombus formation and hemostasis, platelets are also involved in tissue regeneration following injury and the pathophysiology of inflammation. When platelets are activated by hemostasis and the like, receptors of cell adhesion factors such as Integrin $\alpha IIB\beta 3$ (glycoprotein IIb/IIIa: complex of CD41a and CD61) appear on the membrane thereof. As a result, platelets aggregate with each other and fibrin is clotted by various types of blood coagulation factors released from the platelets resulting in the formation of thrombi.

Platelets purified by the method of the present invention are of high quality. High-quality purified platelets as referred to in the present description refer to platelets that maintain a high level of physiological activity per fraction and have a sufficiently low number of unusual platelets as a result of having substantially removed all megakaryocytes.

The physiological activity of platelets can be evaluated by measuring according to a known method. For example, the number of activated platelets can be measured using antibody to PAC-1, which specifically binds to Integrin αIIBβ3 on the membranes of activated platelets. In addition, the number of activated platelets may also be measured by similarly detecting the platelet activation marker, CD62p (P-selectin), with antibody. For example, the number of activated platelets can be measured by carrying out gating with antibody to activation-independent platelet marker CD61 or CD41 using flow cytometry, followed by detecting binding of anti-PAC-1 antibody and anti-CD62p antibody. These steps may be carried out in the presence of adenosine diphosphate (ADP).

In addition, evaluation of platelet function can be carried out by observing whether or not fibrinogen is bound in the presence of ADP. Activation of integrin required in the early stage of thrombus formation occurs as a result of platelets binding to fibrinogen.

Moreover, evaluation of platelet function can also be carried out by a method involving visualizing the ability to form thrombi in vivo as indicated in FIG. 6 of WO 2011/034073.

On the other hand, platelets are evaluated as having deteriorated or being abnormal in cases in which the expression rate of CD42b or the annexin V positive rate is low. These platelets do not have adequate thrombus formation or hemostasis functions and are not useful clinically.

In the present description, "platelet deterioration" refers to a reduction in CD42b (GPIbα) on the surface of the platelets. Thus, deteriorated platelets include platelets in which expression of CD42b has decreased and platelets in which the extracellular region of CD42b has been cleaved by a shedding reaction. When CD42b is no longer present on the platelet surface, association with von Willebrand factor (VWF) is no longer possible, and as a result thereof, the blood coagulation function of the platelets is lost. Platelet deterioration can be evaluated using the ratio of CD42b negative rate (or number of CD42b-negative particles) to CD42b positive rate (or number of CD42b-positive particles) in a platelet fraction as an indicator. Platelets become increasingly deteriorated the higher the CD42b negative rate relative to CD42b positive rate or the greater the number of CD42b-negative particles relative to CD42b-positive particles. CD42b positive rate refers to the percentage of platelets capable of binding anti-CD42b antibody among all platelets contained in a platelet fraction, while CD42b negative rate refers to the percentage of platelets not capable of binding anti-CD42b antibody among all platelets contained in a platelet fraction.

In the present description, "unusual platelets" refer to platelets in which the negatively charged phospholipid, phosphatidylserine, has become exposed from the inside to the outside of the lipid bilayer. In the body, phosphatidylserine is exposed on the surface of platelets accompanying the activation thereof, and the blood coagulation cascade reaction is known to be amplified by binding of numerous blood coagulation factors thereto. On the other hand, in unusual platelets, a large amount of phosphatidylserine is continuously exposed on the platelet surface, and if these platelets are administered to a patient, can cause an excessive blood coagulation reaction that has the potential to lead to serious diseases such as disseminated intravascular coagulation syndrome. Since annexin V binds to phosphatidylserine, phosphatidylserine on the platelet surface can be detected using a flow cytometer by using the amount of fluorescent-labeled annexin V that binds thereto as an indicator. Accordingly, the number of unusual platelets can be evaluated based on the annexin V positive rate in a platelet fraction, or in other words, based on the percentage or number of platelets bound by annexin. The number of unusual platelets is higher the higher the annexin V positive rate or the larger the number of bound annexin V particles.

Ordinary conditions can be used for culturing megakaryocytes in the present invention. For example, megakaryocytes may be cultured at a temperature of about 35° C. to about 42° C., about 36° C. to about 40° C. or about 37° C. to about 39° C., and at 5% $CO_2$ to 15% $CO_2$ and/or 20% $O_2$.

There are no particular limitations on the medium used when culturing megakaryocytes, and a known medium preferable for producing platelets from megakaryocytes, or a medium complying therewith, can be suitably used. For example, the medium can be prepared by suitably using a medium used to culture animal cells as a basal medium. Examples of basal media include IMDM medium, Medium 199, Eagle's Minimum Essential Medium (EMEM), αMEM medium, Dulbecco's modified Eagle's Medium (DMEM), Ham's F12 medium, RPMI 1640 medium, Fischer's medium, Neurobasal Medium (Life Technologies Inc.) and mixtures thereof.

The medium may contain serum or plasma or may be serum-free. One or more substances, such as albumin, insulin, transferrin, selenium, fatty acids, trace elements, 2-mercaptoethanol, thiolglycerol, monothioglycerol (MTG), lipids, amino acids (such as L-glutamine), ascorbic acid, heparin, non-essential amino acids, vitamins, growth factors, low molecular weight compounds, antibiotics, antioxidants, pyruvic acid, buffers, inorganic salts or cytokines, can also be contained in the medium as necessary. Cytokines refer to proteins that promote hematopoietic differentiation, and examples thereof include vascular endothelial growth factor (VEGF), thrombopoietin (TPO), various types of TPO-like agents, Stem Cell Factor (SCF), ITS (insulin-transferrin-selenium) supplement and ADAM inhibitors. A preferable medium in the present invention is IMDM medium containing serum, insulin, transferrin, selenium, thiolglycerol, ascorbic acid and TPO. The medium may further contain SCF, and may further contain heparin. Although there are no particular limitations on the concentration of each substance, and TPO, for example, can be contained at about 10 ng/mL to about 200 ng/mL or about 50 ng/mL to about 100 ng/mL, SCF can be contained at about 10 ng/mL to about 200 ng/mL or about 50 ng/mL, and heparin can be contained at about 10 U/mL to about 100 U/mL or about 25 U/mL. A phorbol ester (such as phorbol-12-myristate-13-acetate (PMA)) may also be added.

Human serum is preferable in the case of using serum. In addition, human plasma and the like may be used instead of serum. According to the method of the present invention, platelets equivalent to those obtained when using serum can be obtained even when using these components.

A drug-responsive gene expression induction system in the manner of a Tet-on® or Tet-off® system may be used to overexpress a gene or terminate that overexpression. In that case, in the step of overexpression, overexpression can be inhibited by containing a corresponding drug, such as tetracycline or doxycycline, in a medium followed by the removal thereof from the medium.

Since the step of culturing megakaryocytes in the present invention is carried out by suspension culturing, culturing can be carried out in the absence of feeder cells.

The "culture of megakaryocytes" according to the present invention refers to a culture obtained in the above-mentioned culture step, and contains a culture broth containing megakaryocytes and various additives.

The present invention also includes platelets purified with the method according to the present invention.

The method for producing a blood preparation according to the present invention comprises a step of producing a platelet preparation using the method according to the present invention, and a step of mixing the platelet preparation with another component. An example of another component is erythrocytes.

The present invention also includes a blood preparation purified with this method.

Other components contributing to cell stabilization may also be added to the platelet preparation and blood preparation.

All disclosures of patent documents and non-patent documents cited in the present description are incorporated therein in their entirety by reference.

EXAMPLE

Although the following provides a detailed explanation of the present invention based on examples thereof, the present invention is not limited thereto. A person with ordinary skill in the art would be able to modify the present invention to various aspects without deviating from the significance thereof, and all such modifications are included within the scope of the present invention.

1. Production of Immortalized Megakaryocytes 1-1. Preparation of Hematopoietic Progenitor Cells from iPS Cells Human iPS cells (TKDN SeV2: human fetal skin fibroblast-derived iPS cells established using Sendai viruses) were cultured to differentiate into blood cells in accordance with the method described in Takayama, N., et al., J. Exp. Med., 2817-2830 (2010). Namely, human ES/iPS cell colonies were co-cultured with C3H10T1/2 feeder cells in the presence of 20 ng/mL VEGF (R&D Systems, Inc.) for 14 days to produce Hematopoietic Progenitor Cells (HPC). Culturing was carried out under conditions of 20% $O_2$ and 5% $CO_2$ (to apply similarly hereinafter unless specifically indicated otherwise).

1-2. Gene Transfer System

A lentivirus vector system was used for the gene transfer system. Lentivirus vectors are tetracycline-controlled Tet-on® gene expression induction system vectors. The lentivirus vectors were produced by recombining a mOKS cassette of LV-TRE-mOKS-Ubc-tTA-I2G (Kobayashi, T., et al., Cell, 142, 787-799 (2010)) with c-MYC, BMI1 and BCL-xL. The resulting vectors were LV-TRE-c-Myc-Ubc-tTA-I2G, LV-TRE-BMI1-Ubc-tTA-I2G and LV-TRE-BCL-xL-Ubc-tTA-I2G, respectively.

Virus particles were produced by gene transfer to 293T cells with the above-mentioned lentivirus vectors.

BMI1, MYC and BCL-xL genes were transferred to the genome sequence of the target cells by infecting the target cells with the virus particles. These genes were able to be stably transferred to the target cells and then overexpressed by the addition of doxycycline (Clontech Laboratories, Inc., #631311) to the medium.

1-3. Viral Infection of Hematopoietic Progenitor Cells with c-MYC and BMI1

HPC obtained according to the above-mentioned method were seeded at $5\times10^4$ cells/well in a 6-well plate preliminarily seeded with C3H10T1/2 feeder cells to overexpress c-MYC and BMI1 according to the lentivirus method. At this time, 6 wells each were used for one type of cell line. Namely, virus particles were added to the medium to an MOI of 20 and the cells were infected by spin infection (centrifuging for 60 minutes at 32° C. and 900 rpm). This procedure was carried out twice every 12 hours.

The medium used was obtained by adding 50 ng/mL Human thrombopoietin (TPO, R&D Systems, Inc.), 50 ng/mL Human Stem Cell Factor (SCF, R&D Systems, Inc.) and 2 µg/mL Doxycycline (Dox) to a basal medium (IMDM (Iscove's Modified Dulbecco's Medium, Sigma-Aldrich, Inc.) containing 15% Fetal Bovine Serum (GIBCO), 1% Penicillin-Streptomycin-Glutamine (GIBCO), 1% Insulin-Transferrin-Selenium Solution (ITS-G, GIBCO), 0.45 mM 1-Thioglycerol (Sigma-Aldrich, Inc.) and 50 µg/mL L-Ascorbic Acid (Sigma-Aldrich, Inc.)) (the resulting medium being referred to as differentiation medium), followed by the further addition of protamine thereto at a final concentration of 10 µg/mL.

1-4. Production and Maintenance Culturing of Self-Propagating Megakaryocyte Strains Defining the day on which the cells were virally infected with c-MYC and BMI1 according to the above-mentioned method as Infection Day 0, self-propagating megakaryocyte strains were each produced by culturing c-MYC and BMI1 gene-transferred megakaryocytes in the manner described below. Forced expression of BMI1 gene and c-MYC gene was carried out by adding 1 µg/mL of doxycycline (Clontech Laboratories, Inc., #631311) to the medium.

Infection Days 2 to 11

Virally-infected blood cells obtained according to the above-mentioned method were recovered by pipetting, and after removing the supernatant by centrifuging for 5 minutes at 1200 rpm, the cells were re-suspended in fresh differentiation medium and seeded on fresh C3H10T1/2 feeder cells (6-well plate). Subculturing was carried out by performing the same procedure on Infection Day 9. After counting the number of cells, the cells were seeded on C3H10T1/2 feeder cells at $1\times10^5$ cells/2 mL/well (6-well plate).

Infection Days 12 to 13

The same procedure was carried out as that performed on Infection Day 2. After counting the number of cells, the cells were seeded on C3H10T1/2 feeder cells at $3\times10^5$ cells/10 mL/100 mm dish (100 mm dish).

Infection Day 14

The virus-infected blood cells were recovered and reacted with antibody using 2 µL, 1 µL and 1 µL aliquots of anti-human CD41a-APC antibody (BioLegend, Inc.), anti-human CD42b-PE antibody (eBioscience) and anti-human CD235ab-pacific blue antibody (BioLegend, Inc.), respectively, per $1.0\times10^5$ cells. Following the reaction, the cells were analyzed using FACS Verse (Becton, Dickinson and Company). On Infection Day 14, those cells having a CD41a-positive rate of 50% or more were designated as self-propagating megakaryocyte strains.

1-4. Viral Infection of Self-Propagating Megakaryocytes with BCL-xL

BCL-xL was transferred to the above-mentioned self-propagating megakaryocyte strains on Infection Day 14 according to the lentivirus method. Virus particles were added to the medium to an MOI of 10 and the cells were infected by spin infection (centrifuging for 60 minutes at 32° C. and 900 rpm). Forced expression of BCL-xL gene was carried out by adding 1 µg/mL of doxycycline (Clontech Laboratories, Inc., #631311) to the medium.

1-5. Production and Maintenance Culturing of Immortalized Megakaryocyte Strains

Infections Days 14 to 18

Self-propagating megakaryocyte strains transferred with BCL-xL obtained according to the above-mentioned method were recovered and centrifuged for 5 minutes at 1200 rpm. Following centrifugation, the precipitated cells were suspended in fresh differentiation medium followed by seeding on fresh C3H10T1/2 feeder cells at $2 \times 10^5$ cells/2 mL/well (6-well plate).

Infection Day 18: Subculturing

After counting the number of cells, the cells were seeded at $3 \times 10^5$ cells/10 mL/100 mm dish.

Infection Day 24: Subculturing

After counting the number of cells, the cells were seeded at $1 \times 10^5$ cells/10 mL/100 mm dish. Subculturing was subsequently carried out every 4 to 7 days to carry out maintenance culturing.

Self-proliferating megakaryocyte strains transferred with BCL-xL gene were recovered on Infection Day 24 and subjected to immunostaining using 2 µL, 1 µL and 1 µL aliquots of anti-human CD41a-APC antibody (BioLegend, Inc.), anti-human CD42b-PE antibody (eBioscience) and anti-human CD235ab-Pacific Blue antibody (Anti-CD235ab-PB, BioLegend, Inc.), respectively, per $1.0 \times 10^5$ cells, followed by analyzing the cells using FACS Verse (Becton, Dickinson and Company), and those cells having a CD41a-positive rate of 50% or more on Infection Day 24 as well were designated as an immortalized megakaryocyte strain. These cells able to proliferate on Infection Day 24 and beyond were designated as immortalized megakaryocyte strain SeV2-MKCL.

The resulting SeV2-MKCL cells were static cultured in a 10 cm dish (10 mL/dish). The medium used was obtained by adding the following components to IMDM, which is a basal medium (at a final concentration).

FBS (sigma #172012, Lot. 12E261) 15%
L-Glutamine (Gibco #25030-081) 2 mM
ITS (Gibco #41400-045) 100-fold dilution
MTG (monothioglycerol, sigma # M6145-25 ML) 450 µM
Ascorbic acid (sigma # A4544) 50 µg/mL
Puromycin (sigma # P8833-100 MG) 2 µg/mL
SCF (Wako Pure Chemical Industries, Ltd., #193-15513) 50 ng/mL
TPO-like agent 200 ng/mL
Culturing conditions: 37° C., 5% $CO_2$ 2. Platelet Production Next, overexpression was terminated by culturing in medium not containing doxycycline. More specifically, the immortalized megakaryocyte line (SeV2-MKCL) obtained according to the method of 1 was washed twice with PBS(—) and suspended in the medium for producing platelets described below. The seeding density of the cells was $1.0 \times 10^5$ cells/mL.

Platelets were produced by culturing in platelet production medium for 6 days.

The medium for producing platelets (platelet production medium) was obtained by adding the following components to IMDM, which is a basal medium (at a final concentration).

FBS 15%
L-Glutamine (Gibco #25030-081) 2 mM
ITS (Gibco #41400-045) 100-fold dilution
MTG (monothioglycerol, sigma # M6145-25 ML) 450 µM
Ascorbic acid (sigma # A4544) 50 µg/mL
SCF (Wako Pure Chemical Industries, Ltd., #193-15513) 50 ng/mL
TPO-like agent 200 ng/mL
ADAM inhibitor 15 µM
SR1 750 nM
ROCK inhibitor 10 µM 3. Platelet Purification 3-1. Removal of Megakaryocytes The recovery bag was replaced with a disposable waste bag of the ACP215 disposable kit using a sterile connecting apparatus. The Hicaliq IVH bag (Terumo Corporation, HC-B3006A) was used for the cell bag.

Next, 2.4 L of a culture broth containing megakaryocytes and produced platelets obtained in the platelet production step were prepared. 10% by volume of ACD-A solution was added to the 2.4 L of culture broth. Subsequently, the culture broth to which the ACD-A solution had been added was injected into the cell bag. The Hicaliq IVH bag (Terumo Corporation, HC-B3006A) was used for the cell bag.

Next, the cell bag containing the culture broth was connected to the ACP215 disposable kit using a sterile connecting apparatus.

The ACP215 was started up in the service mode and the centrifuge speed was set to 2000 rpm (223.8×g).

The ACP215 disposable kit was installed in the ACP215 and a cell bag containing medium was placed on the stand.

The ACP215 was started up and culture broth present in the cell bag was injected into the separation bowl at about 100 mL/min. The eluate that eluted from the bowl was recovered in the recovery bag.

After the entire amount of culture broth present in the cell bag was added to the bowl, 500 mL of wash solution were added.

After the wash solution was injected into the separation bowl, centrifugation was discontinued and the recovery bag containing recovery liquid (containing platelets) was separated using a tube sealer.

3-2. Concentration, Washing and Preparation (1) Concentration Step

The recovery bag containing the recovery liquid (containing platelets) was connected to a new ACP215 disposable kit using a sterile connecting apparatus.

The ACP215 was started up in the normal mode. WPC was selected for the program and the ACP215 disposable kit having the above-mentioned recovery bag connected thereto was installed in accordance with the system instructions. Furthermore, the recovery bag containing recovery liquid was placed on the stand.

Next, the centrifugation speed of the ACP215 was changed to 5000 rpm (1398.8×g) and centrifugation was begun.

When the recovery liquid began to be injected into the separation bowl, injection was switched from automatic injection to manual injection. More specifically, recovery liquid was made to be injected into the separation bowl at about 100 mL/min. After the entire amount of recovery liquid had been added to the separation bowl, 500 mL of wash solution were added.

(2) Washing Step

Washing was carried out by washing with 2000 mL of wash solution in accordance with the ACP215 program.

(3) Preparation 200 mL of washed platelets were recovered in a platelet preparation bag in accordance with the ACP215 program.

4. Measurement of Megakaryocyte Count, Platelet Count, Platelet Physiological Activity and Unusual Platelets 4-1. Measurement Method The megakaryocyte count, platelet count, platelet physiological activity and number of unusual platelets were measured in the purified platelet preparation.

In measuring megakaryocyte count, platelet count and platelet physiological activity, 900 µL of diluent were added to a 1.5 mL micro tube followed by the addition of 100 µL of the megakaryocyte culture or the recovered product following platelet purification and mixing. 200 µL of the resulting solution were dispensed into a FACS tube followed by the addition of labeled antibody and staining.

In measuring the number of unusual platelets, 100 µL of the megakaryocyte culture or recovered product following platelet purification were dispensed into an FACS tube, followed by adding labeled antibody and protein, staining and analyzing by flow cytometry after diluting 5-fold with annexin V binding buffer (BD) immediately prior to analysis.

The Antibodies Used are Indicated Below.

(1) Measurement of megakaryocyte count and platelet count 1.0 µL anti-CD41a antibody, APC label (Bio Legend 303710)

1.0 µL a anti-CD42a antibody, PB label (eBioscience 48-0428-42)

1.0 µL a anti-CD42b antibody, PE label (Bio Legend 393906)

(2) Measurement of Platelet Physiological Activity 0.5 µL anti-CD42a antibody, PB label (eBioscience 48-0428-42)

0.5 µL anti-CD42b antibody, PE label (Bio Legend 303906)

0.5 µL anti-CD62p antibody, APC label (Bio Legend 304910)

10 µL anti-PAC-1 antibody, FITC label (BD 303704)

(3) Measurement of Number of Unusual Platelets 1.0 µL anti-CD41a antibody, APC label (Bio Legend 303710)

1.0 µL a anti-CD42b antibody, PE label (Bio Legend 303906)

5 µL Annexin V, FITC label (BD 556419)

4-2. Megakaryocyte Count and Platelet Count Measurement Results

The number of CD41a-positive and CD42b-positive particles was defined as the platelet count and the number of positive particles was defined as the megakaryocyte count. The number of platelets and the number of megakaryocytes contained in the culture prior to purification (culture cultured for 6 days using Versus) and the recovered product following purification, respectively, were measured.

The results are shown below and in FIG. 1.

TABLE 1

|  | Before Purification (2600 mL) | After Purification (200 mL) | Yield (%) |
| --- | --- | --- | --- |
| Platelets | $2.40 \times 10^{10}$ | $7.41 \times 10^9$ | 30.8 |
| Megakaryocytes | $6.91 \times 10^8$ | $1.60 \times 10^7$ | 3.3 |

It can be understood from Table 1 that the platelet yield was 30.8%. In addition, megakaryocyte count decreased to 2.3% that prior to purification (megakaryocyte removal rate: 97.7%). Platelet recovery rate increased 3-fold as compared with conventional methods (method using a filter and centrifugal separation method using a centrifuge tube).

4-3. Platelet Physiological Activity Measurement Results

Platelets were stimulated at room temperature with 0.2 µM PMA (Phorbol 12-myristate 13-acetate, sigma # P1585-1 MG) or 100 µM ADP (sigma # A2754) or 0.5 U/mL Thrombin (sigma). Platelet physiological activity was measured with FACS Verse (Becton, Dickinson and Company) 30 minutes after the start of stimulation.

The PAC-1 positive rate and CD62p (p-selectin) positive rate in the CD42a-positive platelet fraction were measured to make a comparative evaluation of physiological activity.

Figure 2:
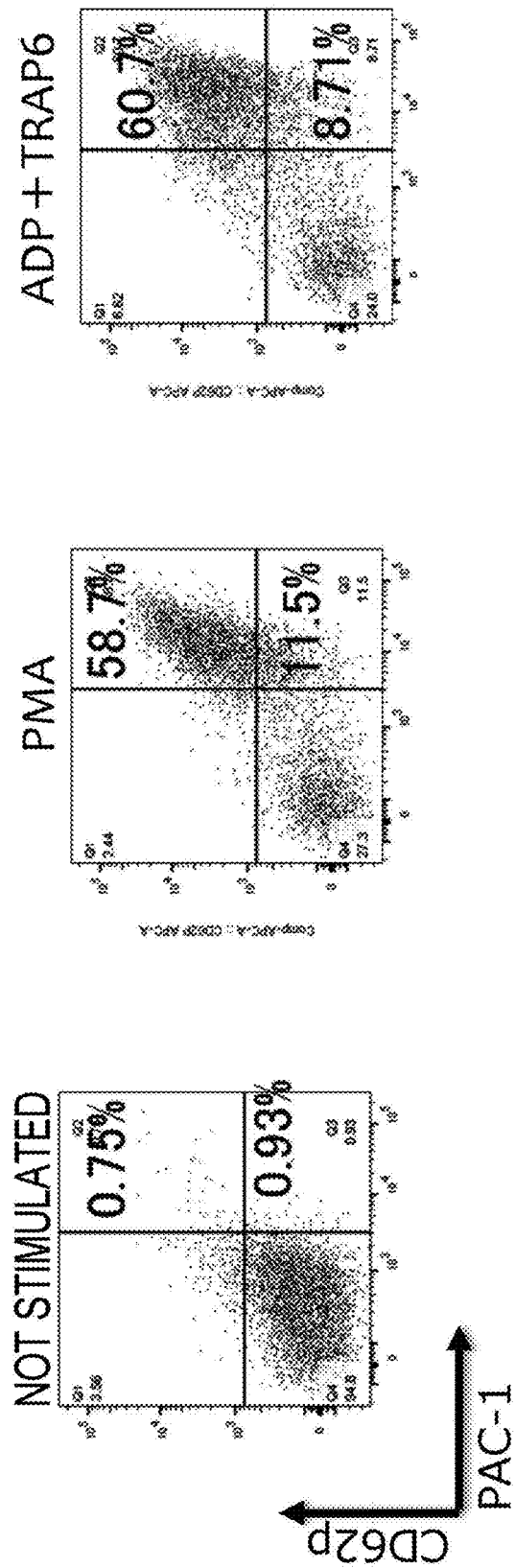
FIG. 2 indicates the results of measuring the physiological activity of platelets following purification by the purification method according to the present invention.

The results are shown in FIG. 2. PAC-1 positive rate and CD62p (p-selectin) positive rate increased following stimulation, and the purified platelets were confirmed to maintain a high level of physiological activity.

4-4. Unusual Platelet Measurement Results

Figure 3:
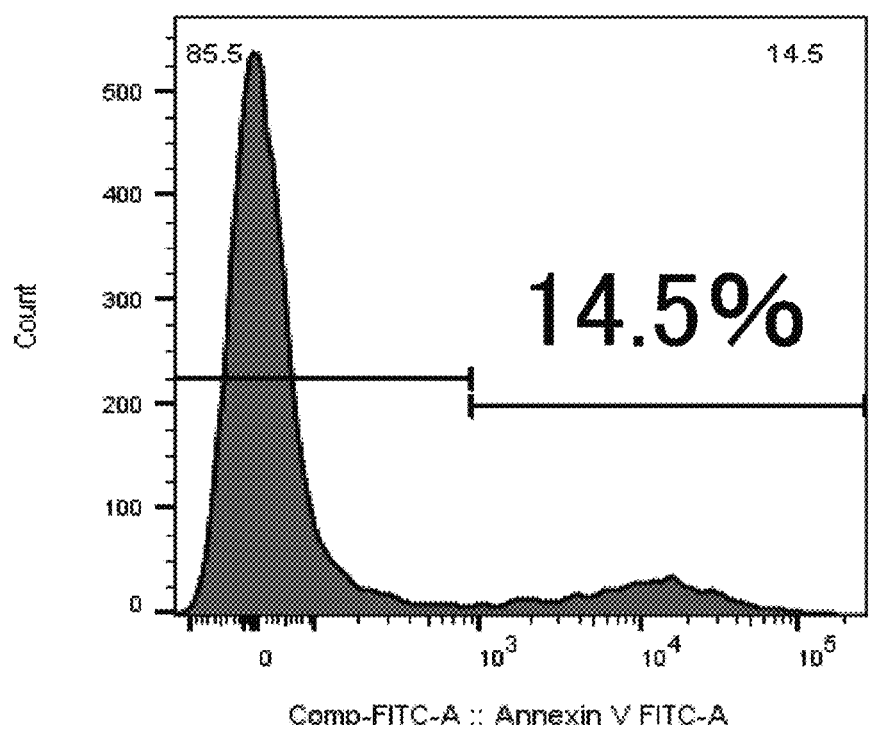
FIG. 3 indicates the results of measuring the percentage of unusual platelets following purification by the purification method according to the present invention.

The number of particles positive for annexin V was taken to indicate the number of unusual platelets. The results are shown in FIG. 3.

Annexin V positive rate was low at 14.5%, indicating that platelet unusualities were adequately inhibited.

4-5. Results of Measuring Platelet Physiological Activity and Unusualities 6 Days after Purification Platelet physiological activity and unusualities were measured 6 days after purification using the same methods as described in the above-mentioned sections 3-2 and 3-3.

Figure 4:
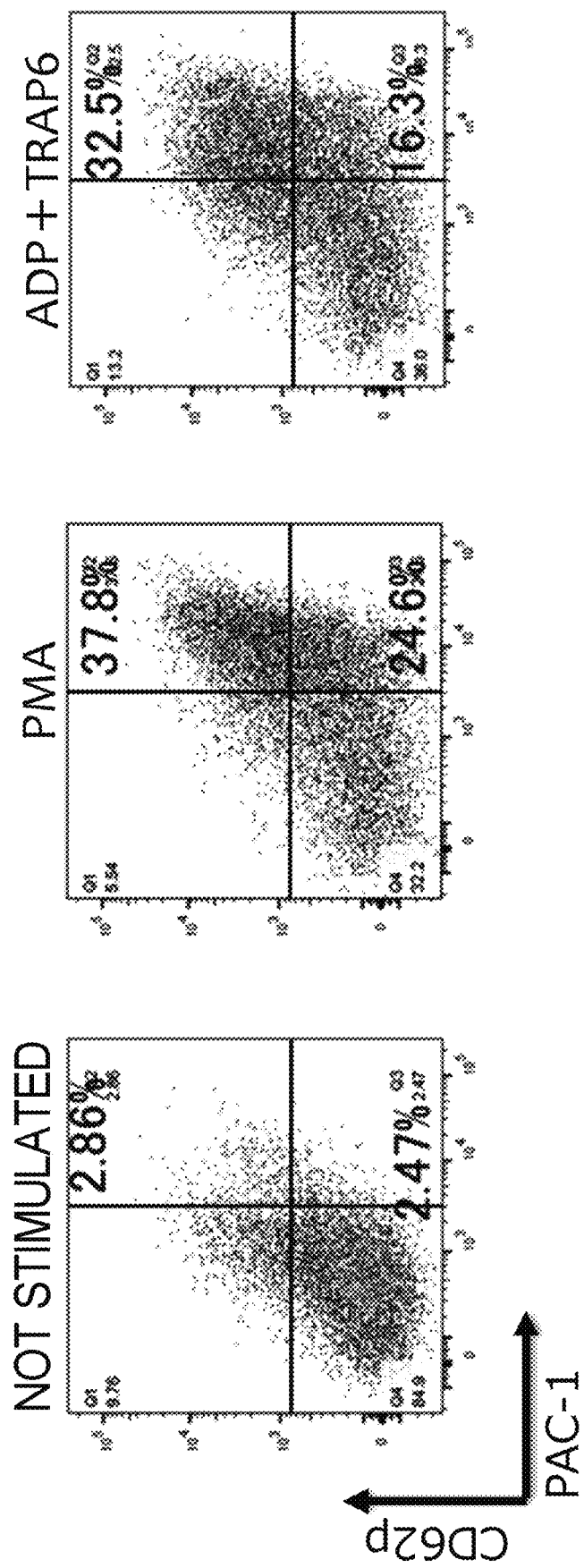
FIG. 4 indicates the results of measuring the physiological activity of platelets 6 days after having purified the platelets with the purification method according to the present invention.
Figure 5:
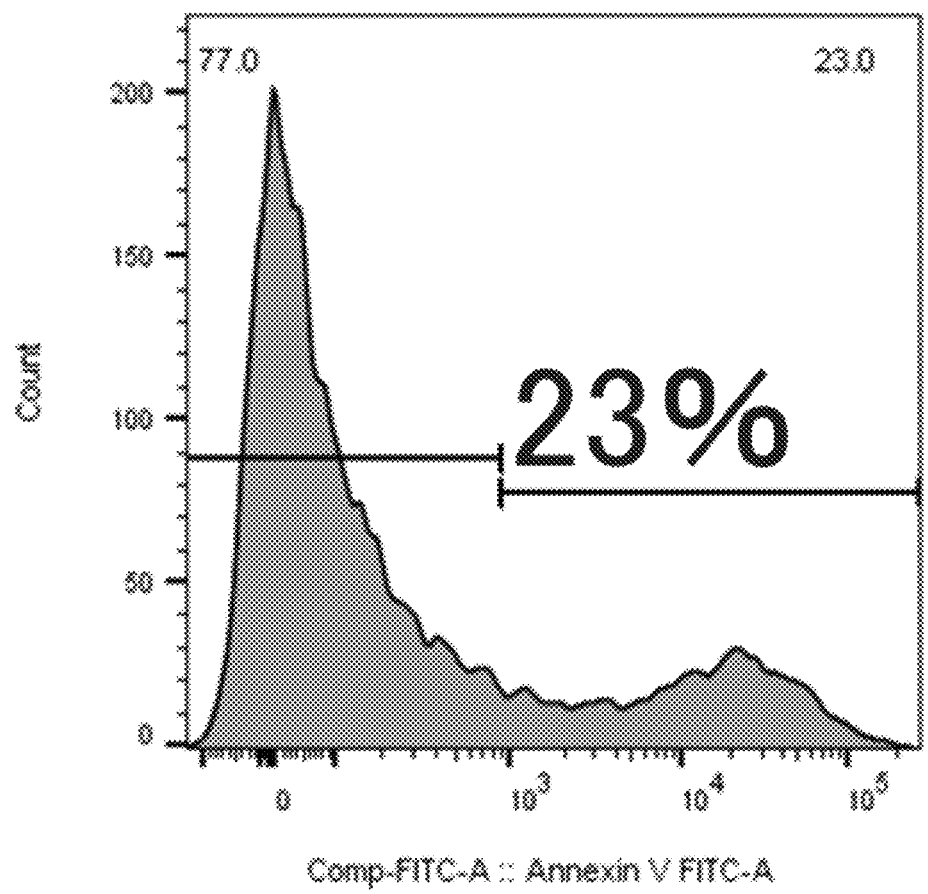
FIG. 5 indicates the results of measuring the percentage of unusual platelets 6 days after having purified the platelets with the purification method according to the present invention.

The results are shown in FIGS. 4 and 5.

Platelet physiological activity was maintained at a high level and the number of unusual platelets was sufficiently low even at 6 days after purification.

What is claimed is:

1. A method for producing purified platelets from a culture of megakaryocytes, comprising:
   removing megakaryocytes from the culture by centrifuging the culture in a first rotatable separation bowl at a centrifugal force of 150×g to 550×g to give a liquid component comprising platelets separated from the megakaryocytes; and
   purifying the platelets in the liquid component by centrifuging the liquid component in a second rotatable separation bowl at a centrifugal force of 600×g to 4000×g.

2. The method according to claim 1, wherein
   the first rotatable separation bowl comprises an outflow port through which the liquid component flows following separation; and
   recovering the liquid component that has flowed out from the outflow port.

3. The method according to claim 2, which further comprises:
   adding a wash solution to the second rotatable separation bowl and then rotating the second rotatable separation bowl; and
   adding a recovery solution and then rotating the second rotatable separation bowl.

4. The method according to claim 2, wherein the culture is injected into the first rotatable separation bowl by allowing the culture to drop therein by gravity.

5. The method according to claim 1, which further comprises
   overexpressing a cancer gene and a Polycomb gene in cells less differentiated than megakaryocytes;
   overexpressing a Bcl-xL gene in the cells; and
   terminating all the overexpression.

6. The method of claim 1, further comprising mixing the purified platelets with another component.

7. A method for producing a platelet composition having increased positive rates of PAC-1 and CD62p compared to platelet compositions purified by centrifuging in a centrifuge tube, which comprises
removing megakaryocytes from a culture of megakaryocytes by centrifuging the culture in a first rotatable separation bowl at a centrifugal force of 150×g to 550×g to give a liquid component comprising platelets separated from the megakaryocytes, and
purifying the platelets in the liquid component by centrifuging the liquid component in a second rotatable separation bowl at a centrifugal force of 600×g to 4000×g.

8. The method according to claim 1, wherein the first and second rotatable separation bowls are the same.

9. The method according to claim 1, wherein the first and second rotatable separation bowls are different.

10. The method according to claim 8, wherein the first rotatable separation bowl is washed before using as the second rotatable separation bowl.

11. The method according to claim 1, which further comprises adding the culture to the first rotatable separation bowl at about 100 mL/min.

12. The method according to claim 1, which further comprises adding the liquid component to the second rotatable separation bowl at about 100 mL/min.

13. A method for producing purified platelets from a culture of megakaryocytes, comprising:
removing megakaryocytes from the culture by centrifuging the culture in a first rotatable separation bowl at a centrifugal force of 150×g to 550×g to give a liquid component comprising platelets separated from the megakaryocytes;
adding a wash solution to the second rotatable separation bowl and then rotating the second rotatable separation bowl;
purifying the platelets in the liquid component by centrifuging the liquid component in a second rotatable separation bowl at a centrifugal force of 600×g to 4000×g; and
adding a recovery solution and then rotating the second rotatable separation bowl.

14. The method according to claim 13, wherein the first and second rotatable separation bowls are the same.

15. The method according to claim 13, wherein the first and second rotatable separation bowls are different.

16. The method according to claim 14, wherein the first rotatable separation bowl is washed before using as the second rotatable separation bowl.

17. The method according to claim 13, which further comprises adding the culture to the first rotatable separation bowl at about 100 mL/min.

18. The method according to claim 13, which further comprises adding the liquid component to the second rotatable separation bowl at about 100 mL/min.

19. The method of claim 13, further comprising mixing the purified platelets with another component.

* * * * *